United States Patent [19]

Aoki et al.

[11] Patent Number: 4,650,515

[45] Date of Patent: * Mar. 17, 1987

[54] DERIVATIVE OF TETRAHYDROBENZOTHIAZOLE AND HERBICIDAL COMPOSITION CONTAINING THE SAME AS ACTIVE INGREDIENT

[75] Inventors: Katsumichi Aoki; Takafumi Shida; Yoichi Kanda; Keigo Satake; Hiroyasu Shinkawa; Shiro Yamazaki, all of Iwaki, Japan

[73] Assignee: Kureha Kagaku Kogyo Kabushiki Kaisha, Tokyo, Japan

[*] Notice: The portion of the term of this patent subsequent to Nov. 6, 2001 has been disclaimed.

[21] Appl. No.: 673,590

[22] Filed: Nov. 21, 1984

Related U.S. Application Data

[62] Division of Ser. No. 491,049, May 3, 1983, Pat. No. 4,577,029.

[51] Int. Cl.[4] .......................................... A01N 43/78
[52] U.S. Cl. ....................................................... 71/90
[58] Field of Search ............................................ 71/90

[56] References Cited

U.S. PATENT DOCUMENTS 4,029,491  6/1977  Krenzer ................................. 71/90
4,045,446  8/1977  Wu ............................... 260/294.8 C

FOREIGN PATENT DOCUMENTS 2123312  12/1971  Fed. Rep. of Germany ........... 71/90
1428157   1/1966  France ..................................... 71/90

OTHER PUBLICATIONS

R. Wegler, Chemic der Planzenschutz—und Schadlingsbekamplungsmiltel, Springer Verlag, Berlin 1971.

Primary Examiner—Robert Gerstl
Attorney, Agent, or Firm—Lyon & Lyon

[57] ABSTRACT

Disclosed herein are the derivatives of tetrahydrobenzothiazole represented by the general formula (I):

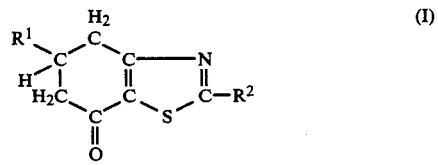

(I)

wherein $R^1$ represents a hydrogen atom, a straight-chain alkyl group having 1 to 6 carbon atoms or branched-chain alkyl group having 1 to 6 carbon atoms, a cycloalkyl group having 3 to 6 carbon atoms or a phenyl group and $R^2$ represents a chemical group selected from the group consisting of:

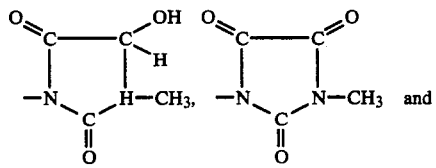

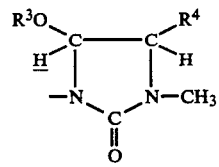

wherein $R^3$ represents a hydrogen atom, a methyl group or an acetyl group and $R^4$ represents a hydrogen atom, a hydroxyl group, methoxy group or acetoxy group and herbicidal compositions containing at least one of the derivatives of tetrahydrobenzothiazole as an active ingredient.

2 Claims, No Drawings

DERIVATIVE OF TETRAHYDROBENZOTHIAZOLE AND HERBICIDAL COMPOSITION CONTAINING THE SAME AS ACTIVE INGREDIENT

This is a division, of application Ser. No. 491,049, filed May 3, 1983, now U.S. Pat. No. 4,577,029.

DETAILED DESCRIPTION OF THE INVENTION

The present invention relates to novel derivatives of tetrahydrobenzothiazole represented by the general formula (I):

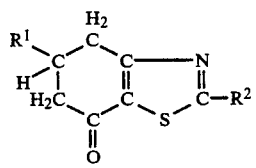

wherein $R^1$ represents a hydrogen atom, a straight-chain alkyl group having 1 to 6 carbon atoms or branched-chain alkyl group having 1 to 6 carbon atoms, a cycloalkyl group having 3 to 6 carbon atoms or a phenyl group and $R^2$ represents a chemical group selected from the group consisting of:

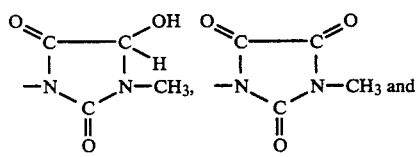

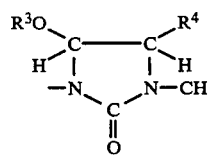

wherein $R^3$ represents a hydrogen atom, a methyl group or an acetyl group and $R^4$ represents a hydrogen atom, a hydroxyl group, methoxy group or acetoxy group and the herbidical compositions containing at least one of the derivatives of tetrahydrobenzothiazole as an active ingredient.

The present inventors have studied for finding a compound showing an excellent activity in selectively controlling weeds such as Echinochloa crus-galli, Poa annua, Stetulaca oleracea, Cardamine flexuosa, Portulaca orelacea, etc. without any phytotoxicity to crop plants such as rice, wheat, soybean and maize, and as a result, they have found that a derivative of 1,2,4-triazole, represented by the general formula (I) shows an excellent herbicidal activity for practically controlling the weeds, and have been attained to the present invention.

Each member of the derivatives of tetrahydrobenzothiazole according to the present invention (hereinafter referred to as the present compound), represented by the general formula (I) exhibited an excellent herbicidal activity when applied onto foliage of graminaceous weeds and broad-leaved weeds in herbicidal tests and accordingly, the field of application of the present compound covers the arable lands such as paddy fields, ordinary crop fields, orchards, etc. and also the non-arable lands.

The present compounds are generally synthesized from each of the following comounds represented by the general formulae (II) and (III):

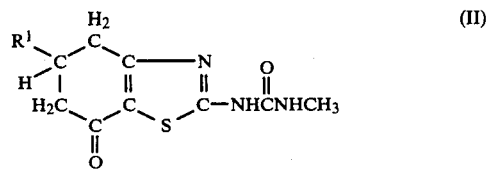

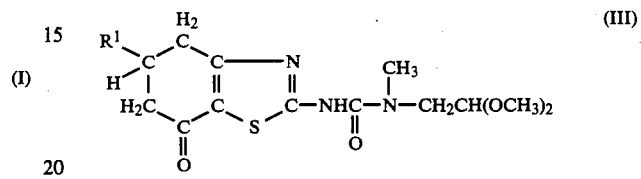

wherein $R^1$ represents the same as in the general formula (I).

The starting compound represented by the general formula (II) is obtained by reacting methyl isocyanate to the amino compound represented by the general formula (IV):

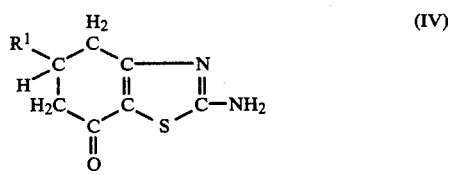

wherein $R^1$ represents the same as in the general formula (I), and the other starting compound represented by the general formula (III) is obtained by reacting phenyl chloroformate with the amino compound represented by the general formula (IV), thereby obtaining a compound represented by the general formula:

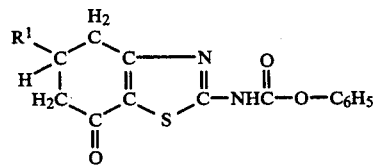

wherein $R^1$ represents the same as in the general formula (I), and reacting the thus obtained phenyl ester with N-2,2-dimethoxyethyl-N-methylamine.

In the cases where the compound represented by the general formula (II) is used as the starting compound, it is brought into reaction with glyoxal, glyoxalic acid or oxalyl chloride to obtain the present compound represented by the general formula (V), (VI) or (VII) shown below.

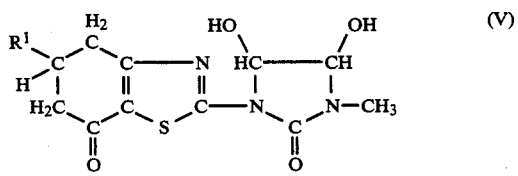

(for instance, Compound No. 1, 5, 13, 20, 23 or 26), wherein $R^1$ represents the same as in the general formula (I).

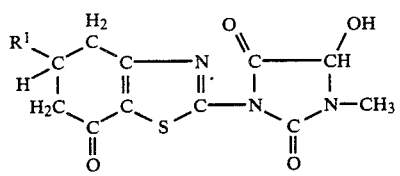 (VI)

(for instance, Compound No. 17), wherein $R^1$ represents the same as in the general formula (I) or

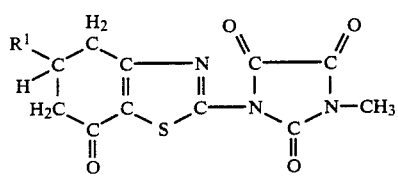 (VII)

(for instance, Compound No. 9, 18, 21, 24 or 27), wherein $R^1$ represents the same as in the general formula (I).

The present compound represented by the general formula (V) can be used for synthesizing other members of the present compounds as follows.

Namely, in the case where methanol is brought into reaction with the compound represented by the general formula (V) and synthesized, the present compound represented by the general formula (VIII):

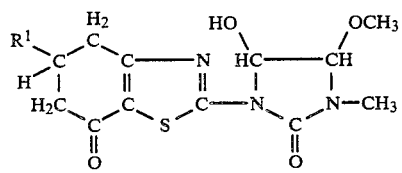 (VIII)

wherein $R^1$ represents the same as in the general formula (I), for instance, Compound No. 6 or 14, is obtained, and further, by acetylating the thus obtained monomethyl ether (VIII), the other present compound represented by the general formula (IX):

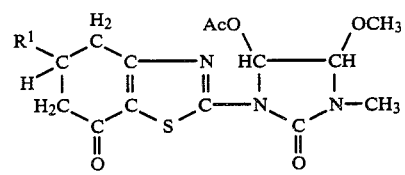 (IX)

wherein $R^1$ represents the same as in the general formula (I), for instance, Compound No. 2, 7 or 15, is obtained.

In addition, by directly acetylating the compound represented by the general formula (V), still another present compound represented by the general formula (X):

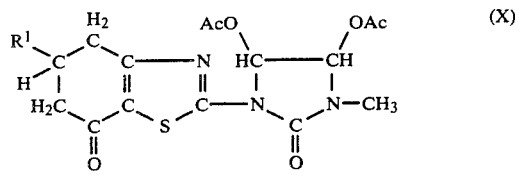 (X)

wherein $R^1$ represents the same as in the general formula (I), for instance, Compound No. 8 or 16 is obtained.

In the case where the compound represented by the general formula (III) is used as the starting compound, it is brought into reaction with a dilute mineral acid to obtain the present compound represented by the general formula (XI):

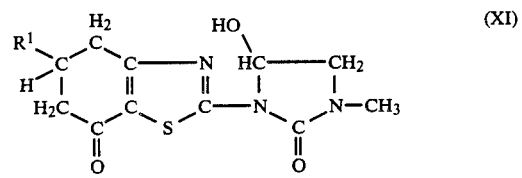 (XI)

wherein $R^1$ represents the same as in the general formula (I), for instance, Compound No. 3, 10, 19, 22 or 25, and further by acetylation of the thus obtained compound (XI) with acetyl chloride, the present compound represented by the general formula (XII):

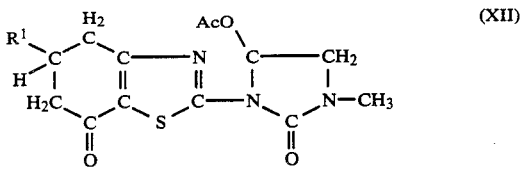 (XII)

wherein $R^1$ represents the same as in the general formula (I), for instance, Compound No. 4 or 12, is obtained, and instead of acetylation, by treating the compound represented by the general formula (XI) with methanol in the presence of a catalytic amount of $H_2SO_4$, the present compound represented by the general formula (XIII):

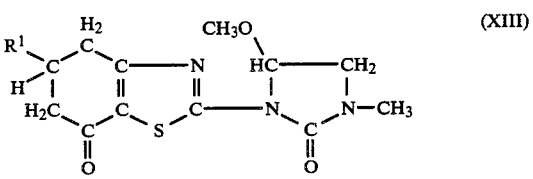 (XIII)

wherein $R^1$ represents the same as in the general formula (I), for instance, Compound No. 11 is obtained.

The concrete examples of the present compounds are shown in Table 1 with the melting point and the process of synthesis thereof, simplified structural formula being given to the heterocyclic group thereof.

TABLE 1

| No. of present compound | Substituent R¹ | Substituent R² | Melting point (°C.) and color Appearance |
|---|---|---|---|
| 1 | H | HO—[N(—)—C(=O)—N(CH₃)]—OH | 210 (decomp.) white crystal |
| 2 | H | AcO—[N(—)—C(=O)—N(CH₃)]—OCH₃ | 122–124 white crystal |
| 3 | CH₃ | HO—[N(—)—C(=O)—N(CH₃)]— | 217–218 (decomp.) white crystal |
| 4 | CH₃ | AcO—[N(—)—C(=O)—N(CH₃)]— | 171–174 white crystal |
| 5 | CH₃ | HO—[N(—)—C(=O)—N(CH₃)]—OH | 195–197 (decomp.) white crystal |
| 6 | CH₃ | HO—[N(—)—C(=O)—N(CH₃)]—OCH₃ | 162–163 white crystal |
| 7 | CH₃ | AcO—[N(—)—C(=O)—N(CH₃)]—OCH₃ | 168–170 white crystal |
| 8 | CH₃ | AcO—[N(—)—C(=O)—N(CH₃)]—OAc | 173–175 white crystal |
| 9 | CH₃ | O=[N(—)—C(=O)—N(CH₃)]=O | 198–200 white crystal |
| 10 | (CH₃)₂CH | HO—[N(—)—C(=O)—N(CH₃)]— | 185–187 white crystal |

TABLE 1-continued

| No. of present compound | Substituent R¹ | Substituent R² | Melting point (°C.) and color Appearance |
|---|---|---|---|
| 11 | (CH₃)₂CH | CH₃O—[N(—)—C(=O)—N(CH₃)]— | 149–150 white crystal |
| 12 | (CH₃)₂CH | AcO—[N(—)—C(=O)—N(CH₃)]— | 154–157 white crystal |
| 13 | (CH₃)₂CH | HO—[N(—)—C(=O)—N(CH₃)]—OH | 172–175 white crystal |
| 14 | (CH₃)₂CH | HO—[N(—)—C(=O)—N(CH₃)]—OCH₃ | 138–140 pale yellow crystal |
| 15 | (CH₃)₂CH | AcO—[N(—)—C(=O)—N(CH₃)]—OCH₃ | 125–128 white crystal |
| 16 | (CH₃)₂CH | AcO—[N(—)—C(=O)—N(CH₃)]—OAc | 122–124 white crystal |
| 17 | (CH₃)₂CH | O=[N(—)—C(=O)—N(CH₃)]—OH | 210–211 white crystal |
| 18 | (CH₃)₂CH | O=[N(—)—C(=O)—N(CH₃)]=O | 188–189 pale yellow crystal |
| 19 | (CH₃)₃C | HO—[N(—)—C(=O)—N(CH₃)]— | 168–170 white crystal |
| 20 | (CH₃)₃C | HO—[N(—)—C(=O)—N(CH₃)]—OH | 188–190 (decomp.) white crystal |

TABLE 1-continued

| No. of present compound | Substituent R¹ | Substituent R² | Melting point (°C.) and color Appearance |
|---|---|---|---|
| 21 | CH₃−C(CH₃)(CH₃)− | −N(C=O,C=O)N−CH₃ (maleimide-type with C=O at top) | 190–191 white crystal |
| 22 | Phenyl | −N(HO)N−CH₃ (with C=O) | 230–231 white crystal |
| 23 | Phenyl | −N(HO,OH)N−CH₃ (with C=O) | 210 (decomp.) white crystal |
| 24 | Phenyl | −N(O=,=O)N−CH₃ (with C=O) | 208–212 white crystal |
| 25 | Cyclohexyl | −N(HO)N−CH₃ (with C=O) | 194–197 white crystal |
| 26 | Cyclohexyl | −N(HO,OH)N−CH₃ (with C=O) | 164–168 (decomp.) white crystal |
| 27 | Cyclohexyl | −N(O=,=O)N−CH₃ (with C=O) | 175–177 yellowish crystal |

Note:
AcO of Compound Nos. 2, 4, 7, 8, 12, 15, 16 mean Acetoxy group

Of the attached drawings, FIGS. 1 to 27 show the infrared absorption spectrum of Compounds Nos. 1 to 27 according to the present invention, respectively.

The following are the synthetic examples of some of the present compounds, the number of each compound corresponding to that shown in Table 1.

Concrete examples of the synthetic process for obtaining the present compound are shown as follows.

SYNTHETIC EXAMPLE 1

Synthesis of
1-(5-t-butyl-4,5,6,7-tetrahydro-7-oxo-2-benzothiazolyl)-4,5-dihydroxy-3-methyl-1,3-imidazolidin-2-one
(Compound No. 20)

Into a solution of 2.0 g (0.0071 mol) of N-(5-t-butyl-4,5,6,7-tetrahydro-7-oxo-2-benzothiazolyl)-N'-methylurea (Compound represented by the general formula (II) wherein R¹ is a t-butyl group) in 50 ml of ethanol, an aqueous 40% solution containing 2.6 g of glyoxal was added, and the mixture was heated under a reflux condenser for 2 hours.

After distilling the solvent from the reaction mixture, the residue was extracted with chloroform, and the extract was washed with water and dried. After distilling chloroform from the dried extract, the residual oily material was solidified with the addition of hexane, and the solid material was washed with ethyl acetate to obtain 2.35 g of crystals melting at 188° to 190° C. with decomposition, in a yield of 98%. IR absorption spectrum and NMR spectrum thereof gave the following data:

IR absorption band (as KBr tablet, cm⁻¹): $\nu_{OH}$ 3250, $\nu_{CO}$ 1710 and 1620. NMR spectrum (DMSO-d₆, ppm) δ: 0.93 (9H, s: H of t-butyl group at 5-position), 1.8 to 3.0 (5H, m: H of 4-(two), 5-(one) and 6-(two) positions), 2.87 (3H, s: H of methyl group at 3'-position), 4.75 (1H, d, J=8 Hz: H at 4'-position), 5.47 (1H, d, J=8 Hz: H at 5'-position), 6.62 (1H, d, J=8 Hz: H of OH at 4'-position) and 7.08 (1H, d, J=8 Hz: H of OH at 5'-position).

SYNTHETIC EXAMPLE 2

Synthesis of
5-hydroxy-4-methoxy-3-methyl-1-(5-methyl-4,5,6,7-tetrahydro-7-oxo-2-benzothiazolyl)-1,3-imidazolidin-2-one
(Compound No. 6)

Into a solution of 3.0 g (0.01 mol) of 4,5-dihydroxy-1-(5-methyl-4,5,6,7-tetrahydro-7-oxo-2-benzothiazolyl)-2-imidazolidinone (Compound No. 1) synthesized from N-(5-methyl-4,5,6,7-tetrahydro-7-oxo-2-benzothiazolyl)-N'-methylurea by the similar procedures to those in Synthetic Example 1 in 30 ml of methanol, 3 drops of conc. H₂SO₄ was added, and the mixture was heated for 1 hour under a reflux condenser. After washing the solid material obtained by distilling methanol from the reaction mixture, with water, the solid material was recrystallized from methanol and further from a mixture of chloroform and hexane to obtain 1.65 g of crystals melting at 162° to 163° C. in a yield of 53%. IR spectral data and NMR spectral data thereof are shown below:

IR absorption band (as KBr-tablet: cm⁻¹): $\nu_{CO}$ 1720 and 1640. NMR spectrum (DMSO-d₆: ppm): δ1.12 (3H, broad s: H of methyl group at 5-position), 2.15 to 2.75 (5H, m: H of 4-(two), 5-(one) and 6-(two) positions), 3.01 (3H, s: H of methyl group at 3'-position), 3.42 (3H, s: H of methoxy group at 4'-position), 4.75 (1H, s: H at 4'-position), 5.07 (1H, broad s: H of OH at 5'-position) and 5.80 (1H, s: H of 5'-position).

SYNTHETIC EXAMPLE 3

Synthesis of
5-acetoxy-1-(5-isopropyl-4,5,6,7-tetrahydro-7-oxo-2-benzothiazolyl)-3-methyl-4-methoxy-1,3-imidazolidin-2-one (Compound No. 15)

After heating a solution of 5 g (0.015 mol) of 1-(5-isopropyl-4,5,6,7-tetrahydro-7-oxo-2-benzothiazolyl)-3-methyl-4,5-dihydroxy-1,3-imidazolidin-2-one (Compound No. 13) obtained by the similar procedures to those in Synthetic Example 1 in 200 ml of anhydrous methanol in the presence of a catalytic amount of conc. H₂SO₄ under a reflux condenser, methanol was distilled off from the reaction mixture, and the residue was extracted with chloroform. After washing the extract with water, the washed extract was subjected to silica-gel column-chromatography to obtain 3 g of purified crystals white in color melting at 138° to 140° C., the thus obtained crystal having been identified to be Compound No. 14 represented by the general formula (I) wherein $R^1$ is an isopropyl group; $R^3$ is a hydrogen atom and $R^4$ is a methoxy group by IR absorption bands thereof at 3400, 1730, 1632 and 1365 cm$^{-1}$.

Into an ice-cooled solution of 3 g (0.009 mol) of the thus obtained crystals of Compound No. 14 in 50 ml of pyridine, 0.83 g (0.01 mol) of acetyl chloride was added drop by drop followed by stirring for 10 min. Then, after stirring the reaction mixture for 2 hours at a room temperature, pyridine was distilled off from the mixture and the residue was extracted with chloroform. After washing the extract with water, the washed extract was subjected to silica-gel column chromatography to obtain 0.4 g of purified white crystals melting at 125° to 128° C. The thus obtained crystalline product was identified as the object compound No. 15 by analysis of NMR spectrum thereof as follows:

NMR Spectrum (CDCl$_3$, ppm) δ: 1.0 (6H, d, J=6 Hz: H of two methyl groups of isopropyl group at 5-position), 1.46 to 2.91 (6H, m: H of 4-(two), 5-(one) and 6-(two) positions and H of isopropyl group, other than those of two methyl groups, at 5-position), 2.17 (3H, s: H of COCH$_3$ at 5'-position), 3.04 (3H, s: H of methyl group to N at 3'-position), 3.58 (3H, s: H of methoxy group at 4'-position), 4.71 (1H, s: H at 4'-position) and 6.81 (1H, s: H at 5'-position).

SYNTHETIC EXAMPLE 5

Synthesis of
4-hydroxy-1-(5-isopropyl-4,5,6,7-tetrahydro-7-oxo-2-benzothiazolyl)-3-methyl-1,3-imidazolidin-2,5-dione
(Compound No. 17)

A mixture of 2.7 g (0.01 mol) of N-methyl-N'-(5-isopropyl-4,5,6,7-tetrahydro-7-oxo-2-benzothiazolyl)urea (Compound represented by the general formula (II) wherein $R^1$ is an isopropyl group), 1.2 g (0.013 mol) of glyoxalic acid monohydrate and 25 ml of benzene was heated for 2 hours under a reflux condenser while removing the azeotropically distilled water. After cooling the reaction mixture, the separated crystals were collected by filtration, washed with water and recrystallized from a mixture of benzene and ethanol to obtain 1.6 g of crystals melting at 210° to 211° C., in a yield of 47%. IR absorption bands and NMR spectrum thereof are shown below:

IR absorption bands (as KBr tablet, cm$^{-1}$): $\nu_{OH}$ 3320, $\nu_{CO}$ 1800, 1740 and 1660. NMR spectrum (DMSO-d$_6$, ppm): δ0.92 (6H, d, J=6 Hz: H of methyl group of isopropyl group at 5-position), 1.48 to 3.41 (6H, m: H of 4-, 5- and 6-positions and H of CH of isopropyl group at 5-position), 2.90 (3H, s: H of methyl group at 1'-position), 5.18 (1H, d, J=9 Hz: H at 5'-position), and 7.18 (1H, d, J=9 Hz: H of OH at 5'-position).

SYNTHETIC EXAMPLE 6

Synthesis of
5-acetoxy-4-methoxy-3-methyl-1-(5-methyl-4,5,6,7-tetrahydro-7-oxo-2-benzothiazolyl)-1,3-imidazolidin-2-one
(Compound No. 7)

After adding 1.1 g (0.0035 mol) of Compound No. 6 synthesized in Synthetic Example 2 to a mixture of 10 ml of acetic anhydride and 0.95 g of sodium acetate, the mixture was heated for 1.5 hours under a reflux condenser. Then, the reaction mixture was poured into iced water and the thus separated crystals were collected by filtration, washed with water and then recrystallized from ethanol to obtain 0.96 g of a crystalline product melting at 168° to 170° C. in a yield of 80%.

IR spectral data and NMR spectral data of the thus obtained compound are shown below: IR absorption band (as KBr tablet, cm$^{-1}$): $\nu_{CO}$ 1730 and 1650. NMR spectrum (DMSO-d$_6$, ppm) δ1.21 (3H, broad d, J=4 Hz: H of methyl group at 5-position), 1.93 (1H, m: H at 5-position), 2.10 (3H, s: H of OCOCH$_3$ at 5'-position), 2.30 to 2.70 (4H, m: H of 4- and 6-positions), 3.01 (3H, s: H of methyl group at 3'-position), 3.55 (3H, s: H of methoxy group at 4'-position), 4.63 (1H at 4'-position) and 6.73 (1H, s: H at 5'-position).

SYNTHETIC EXAMPLE 7

Synthesis of
4,5-diacetoxy-3-methyl-1-(5-methyl-4,5,6,7-tetrahydro-7-oxo-2-benzothiazolyl)-1,3-imidazolidin-2-one
(Compound No. 8)

To 20 ml of acetic anhydride, 2.0 g (0.0067 mol) of 4,5-dihydroxy-3-methyl-1-(5-methyl-4,5,6,7-tetrahydro-7-oxo-2-benzothiazolyl)-1,3-imidazolidin-2-one (Compound No. 5) produced by the similar procedures to those in Synthetic Example 1 and 3 drops of conc. H$_2$SO$_4$ were added, and the mixture was stirred for 30 min at 60° C. Then, the reaction mixture was poured into ice water, and the thus separated crystals were collected by filtration and recrystallized from methanol to obtain 1.5 g of white crystals melting at 173° to 175° C., in a yield of 66%. IR spectral data and NMR spectral data thereof are shown below:

IR absorption bands (as KBr-tablet, cm$^{-1}$): $\nu_{CO}$ 1730 and 1650. NMR spectrum (CDCl$_3$, ppm): δ1.20 (1H, broad d, J=4 Hz: H of methyl group at 5-position), 2.15 (6H, s: H of two acetoxy groups at 4'- and 5'-positions), 2.30 to 2.85 (5H, m: 4-(two), 5-(one) and 6-(two) positions), 3.02 (3H, s: H of methyl group at 3'-position), 6.06 (1H, s: H at 4'-position) and 6.85 (1H, s: H at 5'-position).

SYNTHETIC EXAMPLE 8

Synthesis of
5-hydroxy-3-methyl-1-(5-methyl-4,5,6,7-tetrahydro-7-oxo-2-benzothiazolyl)-1,3-imidazolidin-2-one
(Compound No. 3)

(8-1) Preparation of the starting compound represented by the general formula (III):

Into a suspension of 8.7 g (0.03 mol) of phenyl 5-methyl-4,5,6,7-tetrahydro-7-oxo-2-benzothiazolylcarbamate (Compound represented by the general formula (V) wherein $R^1$ is a methyl group) in 50 ml of DMF, 5.1 g (0.04 mol) of N-2,2-dimethoxyethyl-N-methylamine was added, and the mixture was stirred for 3 hours under a reflux condenser. After distilling DMF from the reaction mixture, the residue was dissolved in chloroform, and the solution was washed with an aqueous 10% solution of sodium carbonate and then with water. By distilling chloroform from the washed solution, pale yellow crystals melting at 226° C. with decomposition were obtained in an amount of 5.6 g.

The thus obtained crystalline substance was identified as the compound represented by the general formula (III) wherein $R^1$ is a methyl group according to IR absorption bands (as KBr-tablet) of 3410, 3160, 1750 and 1660 cm$^{-1}$ thereof.

(8-2) Synthesis of Compound No. 3:

A solution of 5.6 g (0.017 mol) of the thus obtained starting compound in a mixture of 35 ml of ethanol and 47 ml of an aqueous 8.8% solution of hydrogen chloride was heated for 30 min under a reflux condenser and then cooled to a room temperature. The thus separated crystals were collected by filtration, washed with water and gain washed with warm acetone to obtain 1.8 g of white crystals melting at 217° to 218° C. with decomposition. The thus obtained crystalline substance was identified as Compound No. 3 according to the NMR spectral data thereof as follows:

NMR spectrum (d-DMSO, ppm) δ: 1.13 (3H, broad d: H of methyl group at 5-position), 1.5 to 2.73 (5H, m: H of 4(two)-, 5(one)- and 6(two)-positions), 2.87 (3H, s: H of methyl group at 3'-position), 3.32 (1H, dd, J=3 Hz, 11 Hz: H at 4'-position), 5.85 to 6.18 (1H, m: H of OH at 5'-position) and 7.12 (1H, dd, J=3 Hz: 7 Hz: H at 5'-position).

SYNTHETIC EXAMPLE 9

Synthesis of
5-acetoxy-3-methyl-1-(5-methyl-4,5,6,7-tetrahydro-7-oxo-2-benzothiazolyl)-1,3-imidazolidin-2-one
(Compound No. 4)

Into an ice-cooled solution of 2 g (0.007 mol) of 5-hydroxy-3-methyl-1-(5-methyl-4,5,6,7-tetrahydro-7-oxo-2-benzothiazol-2-yl)-1,3-imidazolidin-2-one (Compound No. 3) synthesized in Synthetic Example 8 in 40 ml of pyridine, 0.67 g (0.008 mol) of acetyl chloride was added drop by drop, and the mixture was stirred for 10 min. After additionally stirring the mixture for 2 hours at a room temperature, pyridine was distilled from the mixture and the residue was collected by filtration, washed with water and then recrystallized from ethanol to obtain 1.0 g of white crystals melting at 171° to 174° C. The identification of the thus obtained crystalline substance was carried out according to the NMR spectral data as follows resulting in Compound No. 4:

NMR spectrum (CDCl$_3$, ppm) δ: 1.13 (3H, broad d: H of methyl group at 5-position), 1.68 to 2.85 (5H, m: H̲ at 4-, 5- and 6-positions), 2.1 (3H, s: H of acetyl group at 5'-position), 2.99 (3H, s: N-CH$_3$ at 3'-position), 3.44 (1H, dd, J=3 Hz, 11 Hz: H̲ at 4'-position), 3.92 (1H, dd, J=7 Hz, 11 Hz: H̲ at 4'-position) and 6.96 (1H, dd, J=3 Hz, 7 Hz: H̲ at 5'-position).

SYNTHETIC EXAMPLE 10

Synthesis of
5-hydroxy-3-methyl-1-(5-phenyl-4,5,6,7-tetrahydro-7-oxo-2-benzothiazolyl)-1,3-imidazolidin-2-one
(Compound No. 22)

(10-1) Preparation of the starting compound represented by the general formula (III) wherein R$^1$ is a phenyl group:

To a mixture of 3.6 g (0.01 mol) of phenyl 5-phenyl-4,5,6,7-tetrahydro-7-oxo-benzothiazole-2-ylcarbamate and 1.2 g (0.011 mol) of N-2,2-dimethoxyethyl-N-methylamine, 15 ml of DMF was added, and after heating the whole system for 3 hours at 70° to 80° C., the reaction mixture was condensed, and the product was transferred into benzene. After washing the benzene solution with an aqueous 10% solution of sodium carbonate and drying the washed solution on anhydrous sodium sulfate, benzene was distilled off from the dried solution to obtain the starting compound in crude state.

(10-2) Synthesis of Compound No. 22

The whole amount of the thus obtained starting compound was heated in a mixture of 15 ml of ethanol and 70 ml of an aqueous 5% solution of H$_2$SO$_4$ for 2 hours at 80° C., and the thus separated crystals were collected by filtration. After washing the crystals with water, the crystals were recrystallized from a mixture of 20 ml of acetic acid and 10 ml of DMF to obtain 1.45 g of the colorless crystals melting at 230° to 231° C. in a yield of 42.6%. The thus obtained compound was identified to be Compound No. 22 according to the following IR data and NMR data:

IR absorption bands (KBr-tablet, cm$^{-1}$): $\nu_{OH}$ 3300 and $\nu_{CO}$ 1720, and 1630. NMR spectrum (DMSO-d$_6$, ppm): δ2.63 to 3.94 (7H, m: H of 4(two)-, 5-(one)-, 6(two)- and 4'(two)-positions), 2.87 (3H, s: H of methyl group at 3'-position), 5.98 (1H, t: H of OH at 5'-position), 7.02 (1H, q: H at 5'-position) and 7.40 (5H, d: H of phenyl group).

SYNTHETIC EXAMPLE 11

Synthesis of
1-(5-cyclohexyl-4,5,6,7-tetrahydro-7-oxo-2-benzothiazolyl)-3-methyl-1,3-imidazolidin-2,4,5-trione
(Compound No. 27)

Into 80 ml of chloroform (once washed with water and dried on anhydrous CaCl$_2$), 4 g (0.013 mol) of N-(5-cyclohexyl-4,5,6,7-tetrahydro-7-oxo-2-benzothiazole-2-yl)-N-methylurea (Compound represented by the general formula (II) wherein R$^1$ is a cyclohexyl group) was added, and while gently stirring the mixture, 1.7 ml (0.020 mol) of oxalyl chloride was added at room temperature and the whole system was heated under mild reflux for 70 min to obtain a uniform mixture. After adding 80 ml of petroleum ether to the uniform mixture and leaving the mixture to stand still for one hour at a room temperature, pale yellow crystals separated from the mixture. The crystals were collected by filtration and by adding 80 ml of petroleum ether to the filtrate and leaving the mixture to stand still for a night, additional amount of pale yellow crystals separated. The two portions of the crystals melting at 175°–177° C. when combined weighed 3.7 g, which were identified as the object compound according to the following analytical data:

IR absorption bands (KBr tablet, cm$^{-1}$): 2925, 2850, 1790, 1740, 1660, 1460, 1450 and 1360. NMR spectrum (DMSO-d$_6$, ppm): δ0.63 to 2.97 (16H) and 3.03 (3H, s).

In cases where the present compound represented by the general formula (I) is used for weed-control, the compound may be applied alone or after diluting to a suitable concentration with a diluent as in the application of a conventional herbicidal compound, the diluted material may be applied in a procedure such as spraying and scattering, or it is applicable after admixing with adjuvant(s) such as spreader, wetting agent, sticker, etc.

In addition, since there are no possibility of the decomposition or the denaturation of the present compound when it is admixed with other physiologically active substances nor possibility of decomposing or denaturating such physiologically active substances, the present compound may be used together with the physiologically active substances, for instance, fungicides, bactericides, insecticides, herbicides, plant growth regulators or fertilizers or may be used after admixing with them.

The present invention will be explained more in detail on the preparation of the herbicidal compositions containing the present compound as an active ingredient and on the herbicidal activity of the present compound while referring to the non-limitative examples. In preparing the herbicidal composition, the kinds of the diluents and adjuvants, the ratio of the present compound to the diluents and adjuvants and the kinds of the present compound in the composition can be adopted from a wide range.

FORMULATION EXAMPLE 1

Preparation of a wettable powder

The following components were mixed, and the mixture was well pulverized to obtain a wettable powdery composition. The product, so-called "wettable powder" is used after diluting with water.

50 parts by weight of Compound No. 3
5 parts by weight of a lignisulfonate
3 parts by weight of an alkylsulfonate and
42 parts by weight of diatomaceous earth.

FORMULATION EXAMPLE 2

Preparation of an emulsifiable concentrate

The following components were uniformly mixed together to obtain a composition, so-called "emulsifiable concentrate".

25 parts by weight of Compound No. 10
65 parts by weight of xylene and
10 parts by weight of polyoxyethylene alkyl aryl ether.

The thus prepared "emulsifiable concentrate" is used after diluting with water.

FORMULATION EXAMPLE 3

Preparation of a granular composition

The following components were uniformly mixed together, and after further adding water to the mixture and kneading the moistured mixture, the kneaded material was extruded from an extruding granulator to be granules and dried to be so-called "granule". These "granules" are directly applied onto foliage or soil.

EXAMPLE 1 (HERBICIDAL TEST)

In a planter of the dimensions of 650×210×200 mm soil taken from a crop field was packed to be a plot, and after sowing seeds of the test plant onto the packed soil, the planter was put under cares of plant growing. At the predetermined plant growth stage, an aqueous suspension of one of the present compounds at a concentration of 0.2% by weight, which was obtained by diluting a wettable powder prepared in a similar manner to that in Composition Example 1 with water, was sprayed onto the foliage of the plants in the planter at a rate of 10 liters per are of the soil surface area. After 20 days of spraying, the state of the thus treated plants in the planter was observed to find the degree of phytotoxic symptom on the plants according to the following criteria. The degree of phytotoxic symptom directly corresponds to the herbicidal activity of the herbicide on the plant species. The result of the above-mentioned herbicidal tests is shown in Table 2.

TABLE 2

| No. of compound | Result of Herbicidal Test |  |  |  |  |  |  |  |  |  |
|---|---|---|---|---|---|---|---|---|---|---|
|  | Herbicidal activity |  |  |  |  |  |  |  |  |  |
|  | Plant species |  |  |  |  |  |  |  |  |  |
|  | Weed plants[1] |  |  |  |  | Crop plants[2] |  |  |  |  |
|  | 1 | 2 | 3 | 4 | 5 | 1 | 2 | 3 | 4 | 5 | 6 |
| 5 | 3 | 3 | 5 | 5 | 5 | — | 0 | 0 | — | — | 0 |
| 6 | 3 | 4 | 5 | 5 | 5 | — | 0 | 0 | — | — | 1 |
| 7 | 2 | 3 | 5 | 5 | 5 | — | 0 | 0 | — | — | 0 |
| 8 | 3 | 3 | 5 | 4 | 5 | — | 0 | 0 | — | — | 0 |
| 9 | 3 | 4 | 5 | 5 | 4 | — | 0 | 0 | — | — | 0 |
| 14 | 4 | 5 | 5 | 2 | 5 | — | 2 | 0 | — | — | 0 |
| 16 | 2 | 2 | 5 | 3 | 5 | — | 0 | 0 | — | — | 0 |
| 17 | 3 | 3 | 5 | 3 | 3 | — | 1 | 0 | — | — | 0 |
| 18 | 3 | 2 | 5 | 4 | 5 | — | 0 | 0 | — | — | 0 |
| 19 | 2 | 5 | 5 | 5 | 5 | — | 2 | 0 | — | — | 1 |
| 20 | 3 | 4 | 5 | 5 | 5 | — | 0 | 0 | — | — | 0 |
| 21 | 1 | 1 | 5 | 3 | 5 | — | 0 | 0 | — | — | 0 |
| 22 | 3 | 2 | 5 | 5 | 5 | — | 0 | 0 | — | — | 0 |
| 23 | 3 | 2 | 5 | 3 | 3 | — | 0 | 0 | — | — | 0 |
| 24 | 2 | 3 | 5 | 2 | 5 | — | 0 | 0 | — | — | 0 |
| 25 | 2 | 2 | 3 | 2 | 3 | — | 0 | 0 | — | — | 0 |
| 26 | 2 | 3 | 5 | 2 | 4 | — | 0 | 0 | — | — | 0 |
| 27 | 1 | 2 | 5 | 2 | 5 | — | 0 | 0 | — | — | 0 |

Criteria of evaluating the herbicidal activity
Criteria  Degree of phytotoxicity
0  no phytotoxic symptoms
1  very slight symptoms
2  slight symptoms
3  moderate symptoms
4  severe symptoms
5  withered Note: Name of Plant species tested
[1]Weed plants          [2]Crop plants
1: *Echinocloa crus-galli*    1: Rice
2: *Poa annua*               2: Wheat
3: *Stellaria media*         3: Maize
4: *Portulaca oleracea*      4: Cucumber
5: *Cardamine flexuosa*      5: Tomato
                             6: Soybean

EXAMPLE 2 (HERBICIDAL TEST)

In a planter of the dimensions of 650×210×200 mm, soil taken from a crop field was packed to be a plot, and after sowing seeds of the test plant onto the packed soil, the planter was put under cares of plant growing. At the predetermined plant growth stage, an aqueous suspension of one of the present compounds at a concentration of 0.2% by weight, which was obtained by diluting a wettable powder prepared in a similar manner to that in Composition Example 1 with water, was sprayed onto the foliage of the plants in the planter at a rate of 10 liters per are of the soil surface area. After 20 days of spraying, the state of the thus treated plants in the planter was observed to find the degree of phytotoxic symptom on the plants according to the following criteria. The degree of phytotoxic symptom directly corresponds to the herbicidal activity of the herbicide on the plant species. The result of the abovementioned herbicidal tests is shown in Table 3.

TABLE 3

| No. of compound | Result of Herbicidal Test |  |  |  |  |  |  |  |  |  |
|---|---|---|---|---|---|---|---|---|---|---|
|  | Herbicidal activity |  |  |  |  |  |  |  |  |  |
|  | Plant species |  |  |  |  |  |  |  |  |  |
|  | Weed plants[1] |  |  |  |  | Crop plants[2] |  |  |  |  |
|  | 1 | 2 | 3 | 4 | 5 | 1 | 2 | 3 | 4 | 5 | 6 |
| 1 | 3 | 4 | 5 | 5 | 3 | 1 | 2 | 0 | 5 | 3 | 4 |
| 2 | 4 | 5 | 5 | 3 | 3 | 0 | 1 | 0 | 2 | 3 | 2 |
| 3 | 4 | 4 | 5 | 4 | 5 | 4 | 4 | 4 | 5 | 5 | 5 |
| 4 | 4 | 4 | 5 | 5 | 5 | 4 | 3 | 5 | 5 | 5 | 5 |
| 10 | 5 | 5 | 5 | 5 | 5 | 4 | 5 | 5 | 5 | 5 | 5 |
| 11 | 3 | 5 | 4 | 4 | 5 | 0 | 0 | 0 | 0 | 2 | 2 |
| 12 | 2 | 3 | 5 | 4 | 5 | 4 | 3 | 4 | 4 | 5 | 5 |
| 13 | 3 | 5 | 5 | 3 | 5 | 4 | 3 | 1 | 5 | 5 | 3 |
| 15 | 3 | 4 | 5 | 4 | 5 | 3 | 3 | 5 | 5 | 5 | 4 |

Criteria of evaluating the herbicidal activity
Criteria  Degree of phytotoxicity
0  no phytotoxic symptoms
1  very slight symptoms
2  slight symptoms
3  moderate symptoms

TABLE 3-continued

| 4 | severe symptoms |
| 5 | withered |

Note: Name of Plant species tested (1)Weed plants

1: *Echinocloa crus-galli*
2: *Poa annua*
3: *Stellaria media*
4: *Portulaca oleracea*
5: *Cardamine flexuosa*

(2)Crop plants

1: Rice
2: Wheat
3: Maize
4: Cucumber
5: Tomato
6: Soybean

EXAMPLE 3 (HERBICIDAL TEST)

Herbicidal tests by foliar application of the present compound

To the seedlings of the plants shown below respectively grown from the seeds sown in a field (1 m×1 m), an aqueous suspension containing respective 0.5 and 0.1% by weight of each of the present compound prepared by diluting each of the wettable powders (so-called wettable compositions) prepared as preparation Example 1 and alkylphenolpolyethylene glycolether as a spreader agent was sprayed from a small sprayer at a rate of 10 liters per are of the soil surface to sufficiently wet the foliage of the plants. After 20 days of the treatment, the plants of the remaining treated plants above ground were weight (without drying) and the value thereof represented by A g/unit area was compared with that of the untreated plants represented by B g/unit area.

The results are shown by A/B (%) in Table 4.

TABLE 4

| | No. of compound | | | | | | | | | | | | | | | | | |
|---|---|---|---|---|---|---|---|---|---|---|---|---|---|---|---|---|---|---|
| | 1 | | 2 | | 3 | | 4 | | 10 | | 11 | | 12 | | 13 | | 15 | |
| | Concentration (%) | | | | | | | | | | | | | | | | | |
| Plant | 0.05 | 0.1 | 0.05 | 0.1 | 0.05 | 0.1 | 0.05 | 0.1 | 0.05 | 0.1 | 0.05 | 0.1 | 0.05 | 0.1 | 0.05 | 0.1 | 0.05 | 0.1 |
| *Portulaca oleracea* | 0 | 0 | 13 | 0 | 0 | 0 | 0 | 0 | 0 | 0 | 0 | 0 | 0 | 0 | 0 | 0 | 0 | 0 |
| *Amaranthus lividus* | 0 | 0 | 8 | 0 | 0 | 0 | 0 | 0 | 0 | 0 | 0 | 0 | 14 | 0 | 0 | 0 | 0 | 0 |
| *Chenopodium album* | 0 | 0 | 24 | 5 | 0 | 0 | 0 | 0 | 0 | 0 | 26 | 13 | 11 | 0 | 0 | 0 | 18 | 0 |
| *Glycine max* (Soybean)* | 97 | 95 | 98 | 98 | 95 | 92 | 107 | 99 | 93 | 76 | 88 | 92 | 105 | 99 | 93 | 52 | 93 | 102 |
| *Glycine max* (Soybean)** | 102 | 96 | 97 | 95 | 98 | 96 | 111 | 102 | 88 | 65 | 93 | 87 | 97 | 89 | 85 | 48 | 108 | 99 |

Variety *(Shirome chusei)
**(Toyosuzu)

What is claimed is:

1. A herbicidal composition comprising a herbicidally effective amount of at least one of the derivatives of tetrahydrobenzothiazole represented by the general formula (I):

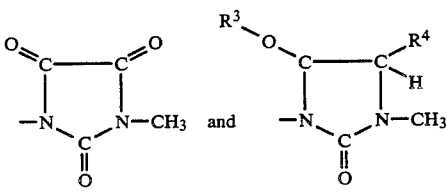

wherein $R^1$ represents a hydrogen atom, a straight-chain alkyl group having 1 to 6 carbon atoms or branched-chain alkyl group having 1 to 6 carbon atoms, a cycloalkyl group having 3 to 6 carbon atoms or a phenyl group and $R^2$ represents a chemical group selected from the group consisting of:

[chemical structures]

wherein $R^3$ represents a hydrogen atom, a methyl group or an acetyl group and $R^4$ represents a hydrogen atom, a hydroxyl group, methoxy group or acetoxy group as an active ingredient and a carrier or a diluent thereof.

2. A herbicidal composition of claim 1, wherein $R^1$ represents t-butyl group, isopropyl group or phenyl group and $R^2$ represents a chemical group selected from the group consisting of:

[chemical structures]

wherein $R^3$ represents a hydrogen atom and $R^4$ represents a hydrogen atom or a hydroxyl group.

* * * * *